(12) United States Patent
Keller et al.

(10) Patent No.: US 7,862,614 B2
(45) Date of Patent: Jan. 4, 2011

(54) INTERVERTEBRAL PROSTHESIS SYSTEM, IN PARTICULAR FOR THE CERVICAL SPINE

(75) Inventors: Arnold Keller, Kayhude (DE); Paul C. McAfee, Baltimore, MD (US)

(73) Assignee: Cervitech, Inc., San Diego, CA (US)

( * ) Notice: Subject to any disclaimer, the term of this patent is extended or adjusted under 35 U.S.C. 154(b) by 1272 days.

(21) Appl. No.: 11/402,002

(22) Filed: Apr. 12, 2006

(65) Prior Publication Data

US 2006/0190082 A1 Aug. 24, 2006

Related U.S. Application Data

(62) Division of application No. 10/356,711, filed on Feb. 3, 2003, now abandoned.

(30) Foreign Application Priority Data

Mar. 12, 2002 (EP) .................................. 02005632

(51) Int. Cl.
*A61F 2/44* (2006.01)
(52) U.S. Cl. ................................................... 623/17.11
(58) Field of Classification Search .... 623/17.11–17.16
See application file for complete search history.

(56) References Cited

U.S. PATENT DOCUMENTS

| 4,085,466 A | * | 4/1978 | Goodfellow et al. | ....... 623/20.3 |
| 4,216,549 A | | 8/1980 | Hillberry et al. | |
| 4,349,921 A | | 9/1982 | Kuntz | |
| 5,236,460 A | | 8/1993 | Barber | |
| 5,258,031 A | | 11/1993 | Salib et al. | |
| 5,306,307 A | | 4/1994 | Senter et al. | |
| 5,314,477 A | | 5/1994 | Marnay | |

(Continued)

FOREIGN PATENT DOCUMENTS

DE 3023353 4/1981

(Continued)

OTHER PUBLICATIONS

Keller, A. et al. U.S. Office Action mailed Aug. 31, 2004, directed to U.S. Appl. No. 10/340,726; 7 pages.

(Continued)

*Primary Examiner*—Anu Ramana
(74) *Attorney, Agent, or Firm*—Jonathan Spangler; Marjorie Jarvis

(57) ABSTRACT

An intervertebral prosthesis system, in particular for the cervical spine, includes at least two types of prostheses. The type of prosthesis includes a first cover plate that is configured to be connected to a first vertebral body, a second cover plate that is configured to be connected to a second vertebral body, and a prosthesis core which is held by a seat on the first cover plate and forms an articulation with the second cover plate. The core of the first type of prosthesis is movable in the anterior-posterior direction relative to the first cover plate. Mobility can also be provided in the lateral direction and rotational direction. The second type of prosthesis of the system may be the same as the first type of prosthesis or may be different, but in all examples of the second type of prosthesis the core is not movable relative to either cover plate.

10 Claims, 1 Drawing Sheet

U.S. PATENT DOCUMENTS

| | | | |
|---|---|---|---|
| 5,360,430 A | | 11/1994 | Lin |
| 5,401,269 A | * | 3/1995 | Buttner-Janz et al. .... 623/17.15 |
| 5,425,773 A | | 6/1995 | Boyd et al. |
| 5,534,029 A | | 7/1996 | Shima |
| 5,676,701 A | | 10/1997 | Yuan et al. |
| 5,865,848 A | | 2/1999 | Baker |
| 5,871,545 A | | 2/1999 | Goodfellow et al. |
| 5,888,223 A | | 3/1999 | Bray, Jr. |
| 6,063,121 A | | 5/2000 | Xavier et al. |
| 6,136,001 A | | 10/2000 | Michelson |
| 6,146,421 A | | 11/2000 | Gordon et al. |
| 6,156,067 A | | 12/2000 | Bryan et al. |
| 6,174,311 B1 | | 1/2001 | Branch et al. |
| 6,190,414 B1 | | 2/2001 | Young et al. |
| 6,228,118 B1 | | 5/2001 | Gordon |
| 6,302,914 B1 | | 10/2001 | Michelson |
| 6,517,580 B1 | | 2/2003 | Ramadan et al. |
| 6,547,823 B2 | | 4/2003 | Scarborough et al. |
| 6,610,093 B1 | | 8/2003 | Pisharodi |
| 6,635,087 B2 | | 10/2003 | Angelucci et al. |
| 6,682,562 B2 | | 1/2004 | Viart et al. |
| 6,770,095 B2 | | 8/2004 | Grinberg et al. |
| 6,936,071 B1 | | 8/2005 | Marnay et al. |
| 7,001,432 B2 | | 2/2006 | Keller et al. |
| 7,267,691 B2 | | 9/2007 | Keller et al. |
| 7,507,242 B2 | * | 3/2009 | Triplett et al. ................. 606/87 |
| 7,637,955 B2 | * | 12/2009 | Marik et al. ............. 623/17.14 |
| 2001/0039454 A1 | | 11/2001 | Ricci et al. |
| 2003/0105527 A1 | | 6/2003 | Bresina |
| 2003/0204260 A1 | | 10/2003 | Ferree |
| 2003/0204261 A1 | | 10/2003 | Eisermann et al. |
| 2004/0002767 A1 | | 1/2004 | Wyss |
| 2004/0093082 A1 | | 5/2004 | Ferree |
| 2004/0127991 A1 | | 7/2004 | Ferree |
| 2004/0133278 A1 | | 7/2004 | Marino et al. |
| 2004/0133281 A1 | | 7/2004 | Khandkar et al. |
| 2005/0256579 A1 | | 11/2005 | Keller et al. |

FOREIGN PATENT DOCUMENTS

| | | |
|---|---|---|
| DE | 29511146 | 1/1996 |
| EP | 0471821 | 2/1992 |
| EP | 0 747 025 | 12/1996 |
| FR | 2718635 | 10/1995 |
| WO | WO-97/20526 | 6/1997 |
| WO | WO 99/65412 | 12/1999 |
| WO | WO 00/53127 | 9/2000 |
| WO | WO 01/01893 | 1/2001 |
| WO | WO 01/64142 | 9/2001 |

OTHER PUBLICATIONS

Keller, A. et al. U.S. Office Action mailed May 27, 2005, directed to U.S. Appl. No. 10/340,726; 6 pages.

Keller, A. et al. U.S. Office Action mailed Apr. 9, 2009, directed to U.S. Appl. No. 11/188,003; 8 pages.

Keller, A. et al. U.S. Office Action mailed Dec. 14, 2009, directed to U.S. Appl. No. 11/188,003; 7 pages.

Keller, A. et al. U.S. Office Action mailed Sep. 14, 2004, directed to U.S. Appl. No. 10/356,711; 7 pages.

Keller, A. et al. U.S. Office Action mailed Jan. 11, 2005, directed to U.S. Appl. No. 10/356,711; 5 pages.

Keller, A. et al. U.S. Office Action mailed Jun. 29, 2005, directed to U.S. Appl. No. 10/356,711; 6 pages.

Keller, A. et al. U.S. Office Action mailed Dec. 12, 2005, directed to U.S. Appl. No. 10/356,711; 6 pages.

Keller, A. et al. U.S. Office Action mailed Jun. 17, 2004, directed to U.S. Appl. No. 10/349,183; 9 pages.

Keller, A. et al. U.S. Office Action mailed Dec. 29, 2004, directed to U.S. Appl. No. 10/349,183; 10 pages.

Keller, A. et al. U.S. Office Action mailed Jun. 13, 2005, directed to U.S. Appl. No. 10/349,183; 9 pages.

Keller, A. et al. U.S. Office Action mailed Mar. 14, 2006, directed to U.S. Appl. No. 10/349,183; 11 pages.

Keller, A. et al. U.S. Office Action mailed Oct. 23, 2006, directed to U.S. Appl. No. 10/349,183; 7 pages.

* cited by examiner

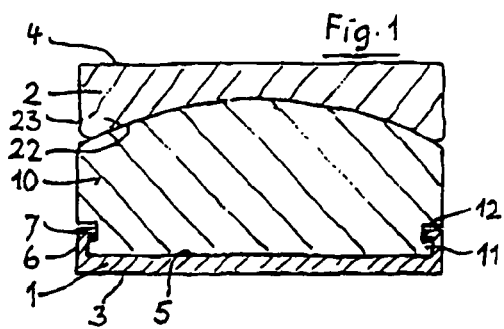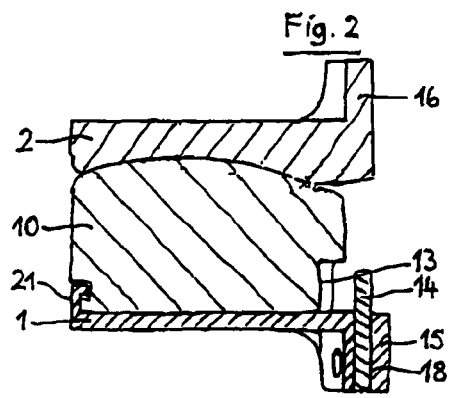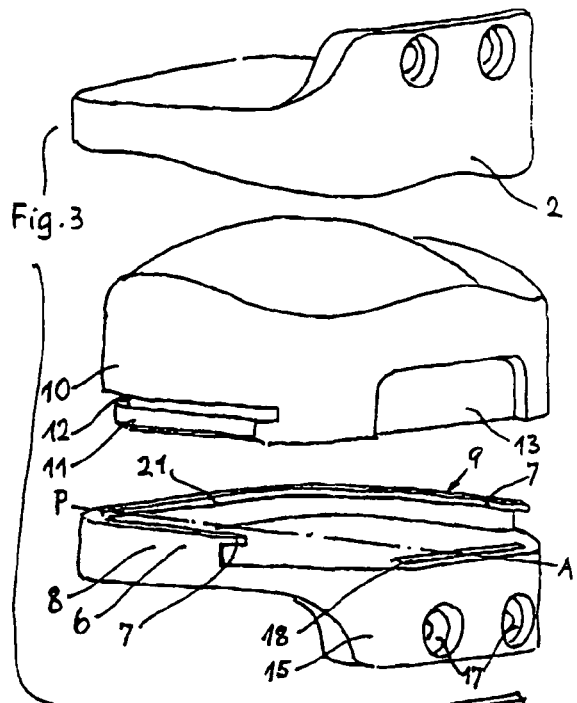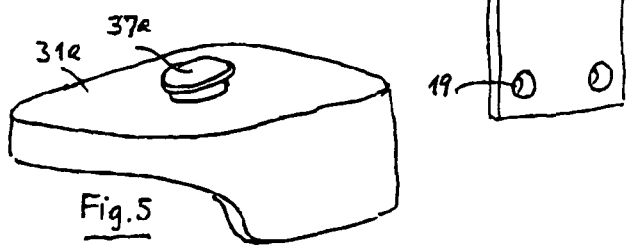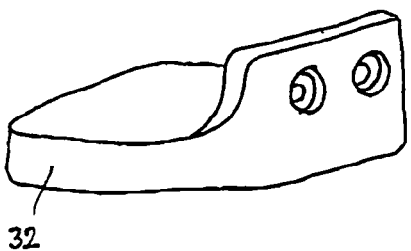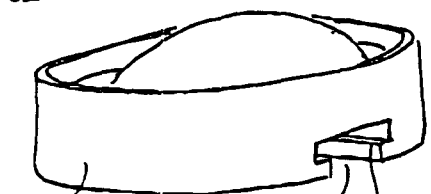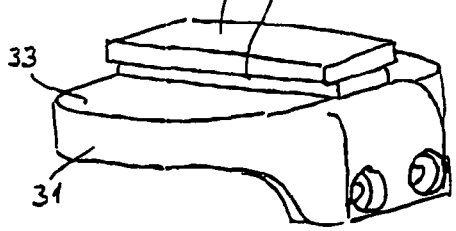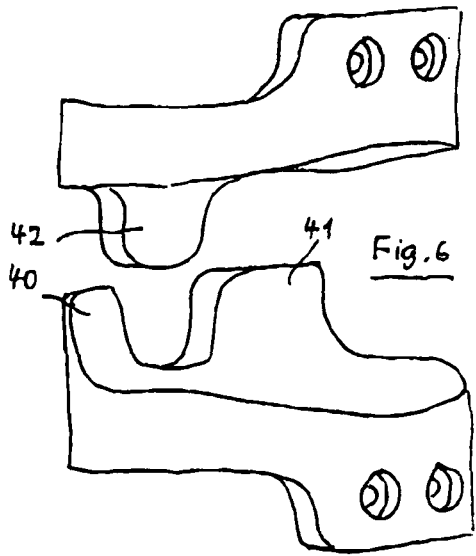

INTERVERTEBRAL PROSTHESIS SYSTEM, IN PARTICULAR FOR THE CERVICAL SPINE

REFERENCE TO RELATED APPLICATION

This application is a division of Ser. No. 10/356,711, filed Feb. 3, 2003, now abandoned, the disclosure of which is incorporated by reference.

FIELD AND BACKGROUND OF THE INVENTION

Intervertebral prostheses are used for replacing the intervertebral disk. They comprise two cover plates, whose outer surfaces are designed for connection to adjacent vertebral bodies, and an articulation device enclosed by the cover plates. In a known prosthesis (EP-B 471 821), the upper cover plate forms a concavely spherical articulation surface on its inner side, which cooperates with the convexly spherical top surface of a prosthesis core of polyethylene in order to form an articulation. The core has a flat underside and a cylindrical edge which are received with matching fit in a seat which is formed on the inside by the lower cover plate.

In order to permit easy flexion movement, it would be useful to choose a small radius of curvature of the articulation surfaces. However, this would lead to a small corresponding surface area of the articulation surfaces and would lessen the capacity for load transmission. In said known prosthesis, the radius of curvature of the articulation surface is chosen approximately equal to half the prosthesis diameter. This has the disadvantage that the prosthesis has a considerable structural height and in many cases cannot be accommodated in the restricted intervertebral space. If, in said type of prosthesis, one were to choose a still greater articulation radius, so that the core assumed the shape of a flat sphere section, it would be found that the articulation properties of the prosthesis leave something to be desired.

SUMMARY OF THE INVENTION

The object of the invention is to make available a prosthesis which has a small structural height and yet has good articulation properties, in particular for use in the cervical spine.

The solution according to the invention lies in providing an intervertebral prosthesis of the type in which the core is movable at least in the AP (anterior-posterior) direction relative to the cover plate forming the seat. Mobility can also be provided in the lateral direction and in rotation. The invention is based on our discovery that, with a comparatively large radius of the articulation surfaces, the articulation movement is associated with a translation movement of the cover plates in relation to one another, the extent of this movement increasing the greater the articulation radius, and that this translation movement is countered by the resistance of the ligament apparatus and the facet articulations acting between the vertebrae.

The invention has recognized that this problem can be overcome by allowing the core to execute a displacement, which compensates for the translation offset of the cover plates relative to one another, in relation to the cover plate holding it. For example, upon a flexion movement relative to the core, the upper cover plate not only pivots about a transverse axis, but also executes a displacement in the ventral direction. This displacement can be compensated by a corresponding dorsal displacement of the core (together with the upper cover plate) relative to the lower cover plate.

The invention also has the advantage that the particular relative position of the upper and lower cover plates can be adapted to the particular anatomical conditions. This applies in particular to those cases where the ventral end faces of the adjacent vertebral bodies determine or influence the position of the cover plates assigned to them and protrude to different extents in the ventral direction.

The core must be held securely in the prosthesis, so that it cannot protrude into the spinal canal for example. For this purpose, movement-limiting devices, which restrict the extent of the movement which the core is allowed, can be provided on one or both cover plates. These movement-limiting devices can interact for example with the outer edge of the core. For example, the lower cover plate can have a raised collar which extends completely or partially around it and which interacts with the outer edge of the core and is so high that the core, even upon a certain expansion of the intervertebral space, cannot slide over it. As is known per se (DE-C 30 23 353), this edge can also be so high in places that it forms projections which engage in corresponding recesses of the opposite cover plate in order to form a cage for retention of the core.

The mobility of the core relative to the cover plate holding it is particularly important in the AP direction because the greatest relative movements (flexion and extension) take place in the sagittal plane, whereas the lateral bending movements are comparatively slight. In an advantageous embodiment of the invention, provision is therefore made for the movement-limiting device to be designed as a guide device in the AP direction. In particular, it can be formed by opposite, parallel lateral guide rails between which the core is held in such a way that it can move only in the AP direction. The guide rails are in this case expediently undercut in order to interact with a ridge of the core which engages in the undercut. In this way, it is ensured that the core does not lift from the cover plate holding it. This has the advantage that the devices provided for restricting the movement of the core do not have to be very high and, for this reason, there is also no risk that they could impede the relative movement of the cover plates with respect to one another. To ensure that the core does not slide out from the rails in the dorsal or ventral direction, suitable limit stops can be provided. The dorsal limit stop is expediently connected rigidly to the cover plate forming the seat (i.e. the guide rails). At the ventral end, a limit stop should be provided which can be removed from its limit-stop position so that the core can be more easily inserted after implantation of the cover plate. The limit stop is then fixed in the position in which it prevents the escape of the core.

Instead of a movement-limiting device which interacts with the outer edge of the core, it is also possible to provide one which interacts with an inner edge of a recess of the core. For example, on the face directed toward the cover plate holding it, the core can have a recess which interacts with a projection on this cover plate. The recess can have an elongate shape extending in the AP direction. In this case, it is expedient to design the articulation to be rotatable about the vertical axis. If the projection is made short in the AP direction or is limited in a circular way in cross section, so that it can pivot in relation to the recess, the core is able to pivot, relative to the cover plate holding it, with respect to the vertical axis, so that a possibility of rotation of the prosthesis articulation about this axis can be dispensed with. This allows for greater freedom in the design of the articulation. If it connects the core pivotably to the upper cover plate, the AP direction of the core is then determined by the AP direction of the upper cover plate.

A particular aspect of the inventive concept resides in the fact that a system of intervertebral prosthesis, in addition to at least one first type of intervertebral prosthesis which have the described AP mobility, also at least one second type of intervertebral prosthesis, preferably of corresponding external configuration, which do not have AP mobility between the prosthesis core and the cover plate holding it. This allows the physician to decide, during the operation, whether or not he wishes to provide AP mobility. The cover plates of the prostheses movable or immovable in the AP direction are expediently of uniform configuration, and only the core is different. However, provision can also be made for the prosthesis core and the cover plate forming the articulation with it to be uniform in all types, while the AP mobility is afforded by differences in the cover plate holding the prosthesis core. Finally, there is also the possibility that all three components are uniform, and that only the limit stop limiting the ventral movement of the prosthesis core in the AP direction is differently located.

Where the terms lower and upper cover plate are used here, this is not intended to imply that the cover plate forming the seat for the core would always have to be arranged at the bottom. Rather, the arrangement can also be chosen the other way round. The claims therefore talk more generally of a first cover plate and a second cover plate.

In order to prevent lifting of the core from the cover plate holding it, provision can be for the projection and the recess to be designed with interacting undercuts.

BRIEF DESCRIPTION OF THE DRAWINGS

Preferred embodiments are explained below with reference to the drawings, in which:

FIG. 1 shows a frontal cross section,
FIG. 2 shows a sagittal cross section,
FIG. 3 shows an exploded view of a first embodiment,
FIG. 4 shows the exploded view of a second embodiment,
FIG. 5 shows a variant of the lower cover plate belonging to the embodiment according to FIG. 4,
FIG. 6 shows two cover plates of a further embodiment without core.

DETAILED DESCRIPTION OF THE INVENTION

The lower cover plate 1 and the upper cover plate 2 of the first embodiment have outer surfaces 3 and 4, respectively, which are intended for anchoring to the associated vertebral body. They are preferably plane. However, other substantially flat configurations including suitable surface structures for better anchoring to the bone are also conceivable. The cover plates are preferably made of metal.

The lower cover plate 1 has a plane upper surface 5 facing toward the upper cover plate 2 and enclosed on three sides by a collar 6 which, above an inner undercut, forms an inwardly projecting ridge 7. The lower cover plate 1 is of approximately rectangular shape in plan view. In the area of its sides 8, 9, the branches of the collar 6 located there extend parallel to one another and rectilinearly.

The upper surface 5 and the collar 6 of the lower cover plate form a seat for the prosthesis core 10, which is made of a material with good sliding properties, for example polyethylene. It has a plane lower surface which matches the surface 5 and which is delimited by an edge ridge 11 above which a groove 12 is situated. The edge ridge 11 engages in the undercut of the collar 6 below the ridge 7. The ridge 7 engages in the groove 12. Sliding play is provided between the collar 6 of the lower cover plate 1 and the edge of the core 10.

The core 10 has the same contour shape as the lower cover plate 1 on both sides (right and left in FIG. 1) and dorsally (left in FIG. 2). The shape of its edge ridge 11 and of its groove 12 exactly follows the shape of the collar 6. Ventrally (right in FIG. 2), the core is slightly shorter than the lower cover plate, so that play remains between its ventral end face 13 and the limit stop 14.

On their ventral edge, the cover plates 1, 2 each have a flange 15, 16 which issues from them approximately at right angles and which has screw holes 17 for fastening to the vertebral body. Located in the flange 15 of the lower cover plate 1 there is a slot 18 in which a limit-stop plate 14 is held displaceably. It can assume the locking position shown in FIG. 2 in which it forms a limit stop for the forwardly directed movement of the core 10. It can also be pushed so far down into the slot 18, or completely removed from the latter, as to allow the prosthesis core to be introduced easily between the cover plates from the ventral direction. It has two bores 19 which, in the locking position of the plate 14, are flush with the screw holes 17. When the lower cover plate 1 is secured on the vertebral body via the screw holes 17, the fastening screws also pass through the holes 19 and thus secure the plate 14 in its locking position.

The lateral branches of the collar 6 form a guide for the prosthesis core, in which guide said prosthesis core can move a certain distance in the AP direction indicated in FIG. 3, namely by the width of the free space between the ventral limit-stop surface 13 of the prosthesis core and the limit-stop plate 14. The ventral part 21 of the collar 6 acts as a securing limit stop which prevents the core from escaping in the dorsal direction from the space between the cover plates 1 and 2. The presence of the undercut on the collar 6 and on the edge of the core 10 is only of importance in the lateral areas 8 and 9 of the lower cover plate 1 and of the core, but not in the dorsal extent 21 of the collar 6.

At its top, the core 10 has a preferably convexly spherical articulation surface 22 which, in order to form an articulation, interacts with the concavely spherical slide surface 23 on the underside of the upper cover plate 2.

Upon flexion movement, the upper cover plate 2 pivots slightly clockwise in relation to the lower cover plate 1 in the view according to FIG. 2, and, upon extension movement, it moves in the opposite direction. If the upper cover plate 2 exactly follows the direction predetermined by the slide surfaces 22, 23, this pivot movement is associated with a translation movement which is directed forwardly upon flexion (toward the right in FIG. 2) and directed rearwardly upon extension (toward the left in FIG. 2). Part of this translation movement may be inconsistent with the physiological situation and may lead to undesired stresses. These stresses cause restoring forces which, in the prosthesis design according to the invention, result in the upper cover plate moving in the opposite direction relative to the lower cover plate and thereby compensating for the undesired component of movement.

Between the interacting guide devices of the core and of the lower cover plate, so much clearance can be left in the lateral direction that a certain relative movement is possible also in this direction.

The extent of the movement clearance in the AP direction is preferably between one and four, more preferably of the order of two to three millimeters. If a relative mobility in the lateral direction is provided, the extent of this should not be more than two millimeters.

In the second embodiment according to FIG. 4, the prosthesis consists of a lower cover plate 31 and of an upper cover plate 32. The lower cover plate has an upper, plane surface 33 on which the prosthesis core 34 lies. Whereas this core in the first embodiment is guided at its outsides, in the second embodiment it has a recess 35 with undercut side edges 36 which interact with an elongate projection 37 of the lower cover plate with correspondingly undercut edges 38. The core 34 is thus movable in the AP direction relative to the lower cover plate 31, in the same way as was explained with reference to the first illustrative embodiment. In addition, the interaction of the undercuts protects it against lifting from the lower cover plate. Suitable limit stops (not shown) can be provided which prevent the prosthesis core from escaping from the space between the plates.

The lower cover plate 31 can be replaced by the lower cover plate 31*a* which is shown in FIG. 5 and which differs from the lower cover plate 31 in that its projection 37*a* is not elongate, but limited in a circular way in plan view. This means that the prosthesis core 34, which is assumed to be connected in terms of rotation to the upper cover plate 32 with respect to a vertical axis, can rotate about the projection 37*a* without impeding the desired AP movement. This may be desirable in the case of an aspherical configuration of the slide surfaces between core and upper cover plate.

This ability of the core to rotate relative to the lower cover plate can also be provided in the embodiment according to FIGS. 1 through 3, by means of the edge 11, 12 of the core 10 being made circular. It can then not only move in the AP direction between the parallel, lateral branches 8, 9 of the collar 6, but can also pivot. Instead of this, it is also possible for both the edge of the prosthesis core and also the collar of the lower cover plate to be made circular. The core is then able to rotate relative to the cover plate, without having mobility in the AP direction.

FIG. 6 shows only the cover plates of a further illustrative embodiment, without the prosthesis core and without the devices which allow the latter to move in the AP direction relative to the lower cover plate. This figure serves merely to demonstrate an embodiment of the means which ensure that a prosthesis core held between the cover plates cannot escape in the dorsal direction. These consist of one or more tongues 40, 41 projecting upward from the lower cover plate, and of one or more tongues 42 projecting downward from the upper cover plate, which tongues are offset relative to one another so that they each engage in the space between or alongside the opposite tongues. The tongues are of such a length in the vertical direction that, even with the greatest possible pivoting of the cover plates, they do not move away from each other to such an extent that the prosthesis core could escape from between them. Corresponding devices can also be provided at the sides and at the ventral end.

The invention claimed is:

1. An intervertebral prosthesis system comprising:
   (a) at least one first type of intervertebral prosthesis comprising a first cover plate configured to be connected to a first vertebral body endplate and comprising a seat, a second cover plate configured to be connected to a second vertebral body endplate, and a first prosthesis core which is held by the seat of the first cover plate and forms an articulation with the second cover plate, the first cover plate, the second cover plate and the first prosthesis core being configured relative to one another so that the first prosthesis core remains movable relative to the first cover plate at least in an anterior-posterior direction relative to the first and second vertebral body endplates after the intervertebral prosthesis system is implanted, wherein the seat comprises a movement-limiting device configured as a guide device with two opposite, parallel lateral guide rails for guiding a displacement of the prosthesis core in the anterior-posterior direction; and
   (b) at least one second type of intervertebral prosthesis having an external configuration corresponding to an external configuration of the first type of intervertebral prosthesis and comprising a third cover plate configured to be connected to a third vertebral body endplate, a fourth cover plate configured to be connected to a fourth vertebral body endplate and a second prosthesis core which is held by a seat on the third cover plate and forms an articulation with the fourth cover plate, wherein the second type of intervertebral prosthesis does not permit anterior-posterior mobility between the second prosthesis core and the third cover plate.

2. The intervertebral prosthesis system according to claim 1, wherein the lateral guide rails are undercut, and the prosthesis core has a ridge engaging in the undercut on the lateral guide rails.

3. The intervertebral prosthesis system according to claim 1, wherein the first cover plate further comprises a dorsal limit stop limiting the movement of the prosthesis core.

4. The intervertebral prosthesis system according to claim 1, wherein the first cover plate further comprises a ventral limit stop that limits the movement of the prosthesis core and is removable from its limit-stop position.

5. The intervertebral prosthesis system according to claim 1, wherein the first prosthesis core has a recess which cooperates with a projection on the first cover plate.

6. The intervertebral prosthesis system according to claim 5, wherein the recess has an elongate shape extending in the anterior-posterior direction.

7. The intervertebral prosthesis system according to claim 5, wherein the projection on the first cover plate and the recess have interacting undercuts formed therein.

8. The intervertebral prosthesis system according to claim 1, wherein the first, second, third and fourth cover plates of the first and second types of intervertebral prostheses are of corresponding uniform external configuration and the first and second prosthesis cores are different.

9. The intervertebral prosthesis system according to claim 1, wherein the second and fourth cover plates and the first and second prosthesis cores of the first and second types are identical and the first and third cover plates are different.

10. The intervertebral prosthesis system according to claim 1, wherein the displacement of the prosthesis core in the anterior-posterior direction is an extent from 1 mm-4 mm.

\* \* \* \* \*